(12) United States Patent
Bertolero et al.

(10) Patent No.: US 7,294,103 B2
(45) Date of Patent: Nov. 13, 2007

(54) RETRACTOR WITH INFLATABLE BLADES

(75) Inventors: Arthur A. Bertolero, Danville, CA (US); Tamer Ibrahim, Pleasant Hill, CA (US)

(73) Assignee: Endoscopic Technologies, Inc., Danville, CA (US)

( * ) Notice: Subject to any disclaimer, the term of this patent is extended or adjusted under 35 U.S.C. 154(b) by 0 days.

(21) Appl. No.: 10/988,000

(22) Filed: Nov. 12, 2004

(65) Prior Publication Data

US 2005/0137460 A1    Jun. 23, 2005

Related U.S. Application Data

(60) Provisional application No. 60/519,512, filed on Nov. 12, 2003.

(51) Int. Cl.
A61B 1/32    (2006.01)

(52) U.S. Cl. .................. 600/207; 600/201; 600/206; 600/208; 600/210; 600/231

(58) Field of Classification Search ........ 600/206–208, 600/210, 233, 201, 231
See application file for complete search history.

(56) References Cited

U.S. PATENT DOCUMENTS

| | | | |
|---|---|---|---|
| 3,782,370 A | | 1/1974 | McDonald |
| 4,183,102 A | | 1/1980 | Guiset |
| 4,984,564 A | * | 1/1991 | Yuen ........................ 600/207 |
| 5,159,921 A | * | 11/1992 | Hoover ...................... 600/207 |
| 5,342,385 A | * | 8/1994 | Norelli et al. ............. 606/193 |
| 5,366,478 A | | 11/1994 | Brinkerhoff et al. |
| 5,520,609 A | * | 5/1996 | Moll et al. ................. 600/204 |
| 5,575,759 A | * | 11/1996 | Moll et al. ................. 600/207 |
| 5,634,883 A | * | 6/1997 | Chin et al. ................. 600/204 |
| 5,634,937 A | | 6/1997 | Mollenauer et al. |
| 5,643,178 A | * | 7/1997 | Moll et al. ................. 600/204 |
| 5,688,223 A | * | 11/1997 | Rosendahl .................. 600/215 |
| 5,716,329 A | | 2/1998 | Dieter |
| 5,730,725 A | * | 3/1998 | Yoon ..................... 604/101.05 |
| 5,730,756 A | * | 3/1998 | Kieturakis et al. ......... 606/190 |
| 5,743,852 A | | 4/1998 | Johnson |
| 5,906,577 A | * | 5/1999 | Beane et al. ............... 600/207 |
| 6,017,305 A | | 1/2000 | Bonutti |

(Continued)

FOREIGN PATENT DOCUMENTS

WO    WO 00/32120    6/2000

*Primary Examiner*—Cary E. O'Connor
*Assistant Examiner*—Jonathan Werner
(74) *Attorney, Agent, or Firm*—James J. Leary; Carol D. Titus; GSS Law Group

(57) ABSTRACT

A surgical retractor is configured to provide surgical access in thoracic surgery, for example through an intercostal incision. The surgical retractor includes at least one inflated or inflatable member to cushion the ribs and surrounding tissue from injury or trauma. In one embodiment, the inflatable member is configured as an inflatable ring with a concave outer surface for engaging and spreading apart two adjacent ribs when the ring is inflated. In another embodiment, the inflatable ring can be combined with a substantially rigid inner ring for supporting and rigidifying the retractor. In yet another embodiment, a plurality of substantially rigid retractor blades is mounted on a spreading track or the like. One or more inflatable members or an inflatable ring are used to cushion the tissue from the rigid retractor blades.

4 Claims, 2 Drawing Sheets

U.S. PATENT DOCUMENTS

| | | | |
|---|---|---|---|
| 6,033,426 A * | 3/2000 | Kaji | 606/213 |
| 6,042,596 A | 3/2000 | Bonutti | |
| 6,142,935 A * | 11/2000 | Flom et al. | 600/206 |
| 6,142,936 A * | 11/2000 | Beane et al. | 600/207 |
| 6,171,236 B1 * | 1/2001 | Bonutti | 600/207 |
| 6,171,299 B1 | 1/2001 | Bonutti | |
| 6,187,023 B1 | 2/2001 | Bonutti | |
| 6,254,533 B1 * | 7/2001 | Fadem et al. | 600/208 |
| 6,312,377 B1 * | 11/2001 | Segermark et al. | 600/232 |
| 6,346,077 B1 * | 2/2002 | Taylor et al. | 600/204 |
| 6,358,266 B1 * | 3/2002 | Bonutti | 606/190 |
| 6,394,951 B1 * | 5/2002 | Taylor et al. | 600/210 |
| 6,440,063 B1 * | 8/2002 | Beane et al. | 600/207 |
| 6,503,265 B1 * | 1/2003 | Fogarty et al. | 606/192 |
| 6,558,371 B2 * | 5/2003 | Dorn | 606/1 |
| 6,709,389 B2 * | 3/2004 | Farascioni | 600/229 |
| 6,736,774 B2 | 5/2004 | Benetti et al. | |
| 2001/0016750 A1 | 8/2001 | Malecki et al. | |
| 2001/0037053 A1 | 11/2001 | Bonadio et al. | |
| 2001/0047188 A1 | 11/2001 | Bonadio et al. | |
| 2003/0078478 A1 | 4/2003 | Bonadio et al. | |
| 2003/0199737 A1 * | 10/2003 | Deslauriers et al. | 600/207 |
| 2004/0154624 A1 | 8/2004 | Bonadio et al. | |

* cited by examiner

RETRACTOR WITH INFLATABLE BLADES

CROSS REFERENCE TO RELATED APPLICATIONS

This application claims the benefit of U.S. Provisional Application No. 60/519,512, filed on Nov. 12, 2003. This and all patents and patent applications referred to herein are hereby incorporated by reference in their entirety.

FIELD OF THE INVENTION

The invention pertains to apparatus and methods for surgical retraction. In particular, it is a retractor with an inflatable retraction member or a cushion to inhibit trauma to the patient's tissues and organs during retraction.

BACKGROUND OF THE INVENTION

Surgery on the heart is one of the most commonly performed types of surgery that is done in hospitals across the U.S. Cardiac surgery can involve the correction of defects in the valves of the heart, defects to the veins or the arteries of the heart and defects such as aneurysms and thromboses that relate to the circulation of blood from the heart to the body. Coronary artery bypass graft (CABG) surgery is one of the most common cardiac surgery procedures. In the past, most cardiac surgery was performed as open-chest surgery, in which a primary median sternotomy was performed. That procedure involves vertical midline skin incision from just below the super sternal notch to a point one to three centimeters below the tip of the xiphoid.

This is followed by scoring the sternum with a cautery, then dividing the sternum down the midline and spreading the sternal edges to expose the area of the heart in the thoracic cavity. This technique causes significant physical trauma to the patient and can require one week of hospital recovery time and up to eight weeks of convalescence. This can be very expensive in terms of hospital costs and disability, to say nothing of the pain to the patient.

Recently, attempts have been made to change such invasive surgery to minimize the trauma to the patient, to allow the patient to recover more rapidly and to minimize the cost involved in the process. New surgical techniques have been developed which are less invasive and traumatic than the standard open-chest surgery. This is generally referred to as minimally-invasive surgery. One of the key aspects of the minimally invasive techniques is the use of a trocar cannula as an entry port for the surgical instruments. In general, minimally invasive surgery entails several steps: (1) at least one, and preferably at least two, intercostal incisions are made to provide an entry position for a trocar; (2) a trocar is inserted through the incision to provide an access channel to the region in which the surgery is to take place, e.g., the thoracic cavity; (3) a videoscope is provided through another access port to image the internal region (e.g., the heart) to be operated on; (4) an instrument is inserted through the trocar channel, and (5) the surgeon performs the indicated surgery using the instruments inserted through the access channel. Prior to steps (1)-(5), the patient may be prepared for surgery by placing him or her on a cardiopulmonary bypass (CPB) system and the appropriate anesthesia, then maintaining the CPB and anesthesia throughout the operation. See U.S. Pat. No. 5,452,733 to Sterman et al. issued Sep. 26, 1995 for a discussion of this technique.

While this procedure has the advantage of being less invasive or traumatic than performing a media, sternotomy, there are numerous disadvantages to using trocars to establish the entry ports for the instruments and viewscope. For example, the trocars are basically "screwed" into position through the intercostal incision. This traumatizes the local tissues and nerve cells surrounding the trocar.

Once in place, the trocar provides a narrow cylindrical channel having a relatively small circular cross-section. This minimizes the movement of the instrument relative to the longitudinal axis and requires specially-designed instruments for the surgeon to perform the desired operation (See, e.g., the Sterman patent U.S. Pat. No. 5,452,733). In addition, because of the limited movement, the surgeon often has to force the instrument into an angle that moves the trocar and further damages the surrounding tissue and nerves. The need to force the instrument causes the surgeon to lose sensitivity and tactile feedback, thus making the surgery more difficult. The surgical retractor of this invention is designed to reduce the initial trauma to the patient in providing access to the internal region, to reduce the trauma to the patient during surgery, to provide the surgeon with greater sensitivity and tactile feedback during surgery, and to allow the surgeon to use instruments of a more standard design in performing the non-invasive surgery.

Other less invasive surgical techniques include access to the region of the heart to be corrected by anterior mediastinotomy or a thoracotomy. In a mediastinotomy, a parasternal incision is made that is two to three inches in length on the left or the right of the patient's sternum according to the cardiac structure that needs the attention in the surgery. Either the third or the fourth costal cartilage is excised depending on the size of the heart. This provides a smaller area of surgical access to the heart that is generally less traumatic to the patient. A thoracotomy is generally begun with an incision in the fourth or fifth intercostal space, i.e. the space between ribs 4 and 5 or ribs 5 and 6. Once an incision is made, it is completed to lay open underlying area by spreading the ribs. A retractor is used to enlarge the space between the ribs.

At the present time, when either of these techniques are used, a retractor is used to keep the ribs and soft tissues apart and expose the area to be operated on to the surgeon who is then able to work in the surgical field to perform the operation. The types of retractors that are used may be seen, for example, in volume 1 of Cardiac Surgery by John W. Kirkland and Brian G. Barratt-Boyes, Second Edition, Chapter 2, at page 101. Commercial-type retractors for minimally-invasive surgery that are useful for a mediastinotomy or a thoracotomy are manufactured by Snowden Pencer (the ENDOCABG rib spreader and retractor), U.S. Surgical (the mini CABG system), and Cardiothoracic Systems (the CTS MIDCAB. System). The ENDOCABG refractor is two opposing retractor arms that are interconnected by a ratchet arm having a thumbscrew which can adjust the distance between the retractor arms. While this provides a useful retractor, it has certain shortcomings in its ease of use. The mini CABG System is an oval-based platform to which a number of retractors are then fitted around the extremity of the universal ring base and adjusted by a gear tooth connection. Each of the retractors have to be separately adjusted and there are other devices that can be connected to the universal base which can aid the surgeon in damping the heart movement to better work on the artery or vessel to which the surgeon is directing his attention. The CTS MIDCAB. System serves a similar function to the ENDOCABG retractor, but is more complex.

Off-pump coronary artery bypass (OPCAB) surgery is a variation of the CABG procedure that is performed on a patient's beating heart. OPCAB surgery can be performed using minimally invasive techniques or using a sternotomy or other thoracotomy for surgical access. A tissue stabilizer is often used for stabilizing an area of tissue on the patient's beating heart to facilitate an anastomosis between the graft vessel and the coronary artery. Examples of tissue stabilizers for OPCAB surgery are described in PCT International Patent Application WO 01/58362 Tissue stabilizer and in U.S. Pat. No. 6,755,780 Method and apparatus for temporarily immobilizing a local area of tissue. Such tissue stabilizers are typically mounted to the surgical retractor or to the surgical table to provide a stable platform for immobilizing the area of tissue.

A disadvantage of current surgical retractors is that they can cause injury or trauma to the tissues surrounding the incision. It would be desirable therefore to provide a surgical retractor that provides convenient surgical access without cause injury or trauma to the surrounding tissues.

SUMMARY OF THE INVENTION

In keeping with the foregoing discussion, the present invention provides a surgical retractor especially adapted for providing surgical access in thoracic surgery, for example through an intercostal incision. The surgical retractor includes at least one inflated or inflatable member to cushion the ribs and surrounding tissue from injury or trauma. In one embodiment, the inflatable member is configured as an inflatable ring with a concave outer surface for engaging and spreading apart two adjacent ribs when the ring is inflated. In another embodiment, the inflatable ring can be combined with a substantially rigid inner ring for supporting and rigidifying the retractor. In yet another embodiment, a plurality of substantially rigid retractor blades is mounted on a spreading track or the like. One or more inflatable members or an inflatable ring are used to cushion the tissue from the rigid retractor blades.

DETAILED DESCRIPTION

Figure 1:
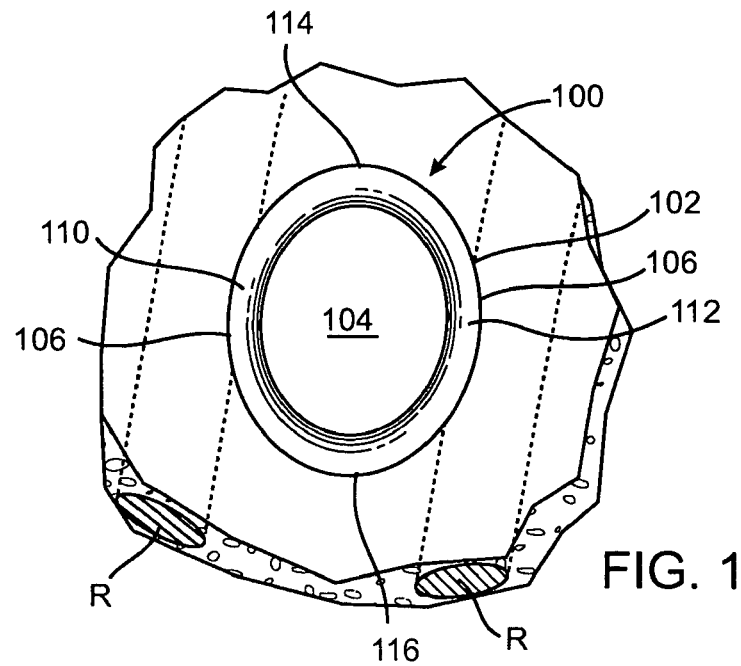
FIG. 1 shows a retractor located within an incision through a patient's skin and tissue.

FIG. 1 shows a retractor located within an incision through a patient's skin and tissue. The retractor is an inflatable ring 102 that assists in creating a space or opening 104, for example between two ribs R during thoracic surgery. The size and shape of the ring 102 may be designed to optimize the resulting opening 104 for a particular surgical procedure, to provide protection for anatomical structures, or to accommodate anatomical limitations.

Figure 2:
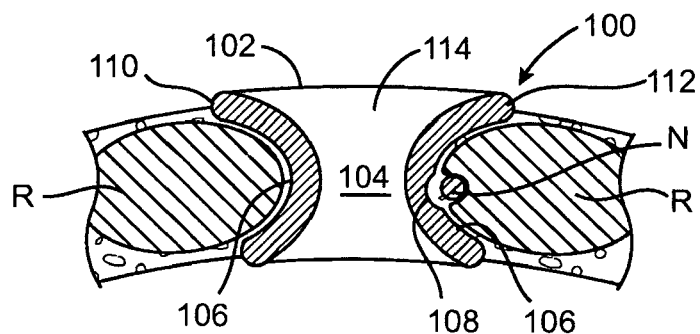
FIG. 2 shows a cross section of the retractor shown in FIG. 1.

FIG. 2 shows a cross section of the retractor 100 shown in FIG. 1. In this case, each side of the inflatable ring 102 of the retractor 100 presses outward on the two adjacent ribs R. The soft, resilient nature of the ring 102 allows the user to create the necessary opening 104 non-traumatically and also provide protection to one or more adjacent nerves, such as the intercostal nerve N, or other sensitive anatomical structures. In this case, the outer surface 106 of the retractor is concave to conform to the shape of the ribs R. The concave outer surface 106 may extend symmetrically all the way around the outside of the inflatable ring 102. Alternatively, the inflatable ring 102 of the retractor may be divided into segments or portions specially configured for their intended purposes. For example, as indicated in FIG. 1, the inflatable ring 102 of the retractor may configured with a first portion 110 having a first concave outer surface 106 for engaging a first rib R and a second portion 112 having a second concave outer surface 106 for engaging a second rib R. A first inflatable column member 114 and a second inflatable column member 116 are positioned between the first portion 110 and the second portion 112 of the inflatable ring 102. The first inflatable column member 114 and the second inflatable column member 116 may have a greater cross sectional area than the first portion 110 and the second portion 112 in order to provide greater force to separate the first rib and the second rib when inflated.

For different applications, the shape of the retractor 100 may be altered into different geometries to protect, inhibit contact with or engage selected portions of the anatomy, such as avoiding pressure on the intercostal nerve. For example, a hole, depression, groove or other opening 108 may be formed in the inflatable member to avoid contact with a particular section of tissue or to provide access during the surgical procedure. Alternately, a bump, ridge or other projection may be present to engage or create a depression in the tissue, such as to inhibit movement of the retractor, etc.

Figure 3:
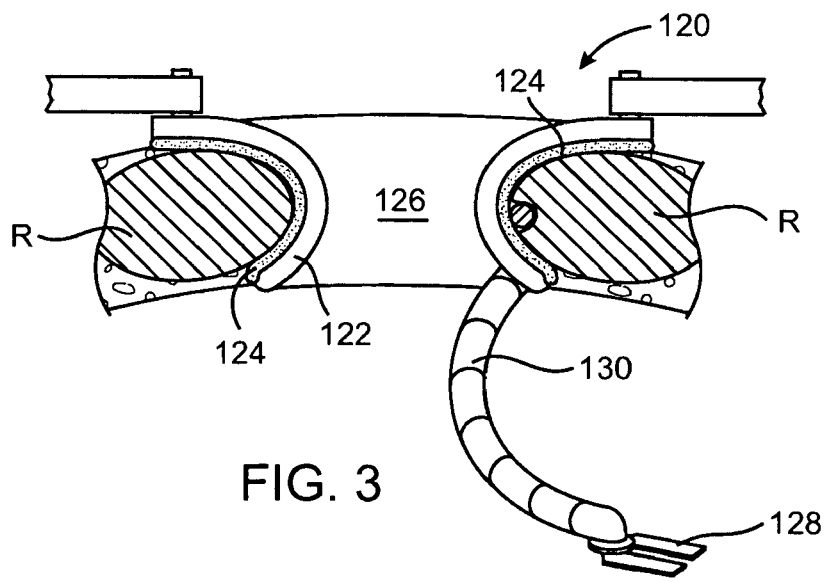
FIG. 3 is a cross section of a second embodiment of the retractor.

FIG. 3 is a cross section of a second embodiment of the retractor 120. In this embodiment, a concave retractor blade or ring 122 is covered with a resilient material or inflatable bladder 124 to non-traumatically create and maintain an opening 126 between a patient's ribs R. The blade 122 or other solid piece of material may be used as a platform to hold other objects, such as a tissue stabilizer, a positioner, a second retractor, an ablation element, syringe or other injection device for injection of drugs or other injectables, etc. A rod or other connecting means 130 may be used to fixedly or adjustably position and secure the surgical or medical tool 128. Adjustment mechanisms may include, but are not limited to, a swivel, a hinge, a malleable member, a ball and socket, a ball and collet, snap-on fittings or other known fixed or adjustable connectors.

In a particularly preferred embodiment, the surgical or medical tool 128 attached to the retractor 120 is a tissue stabilizer for stabilizing an area of tissue on the patient's beating heart for performing an off-pump coronary artery bypass (OPCAB) surgery.

Figure 4:
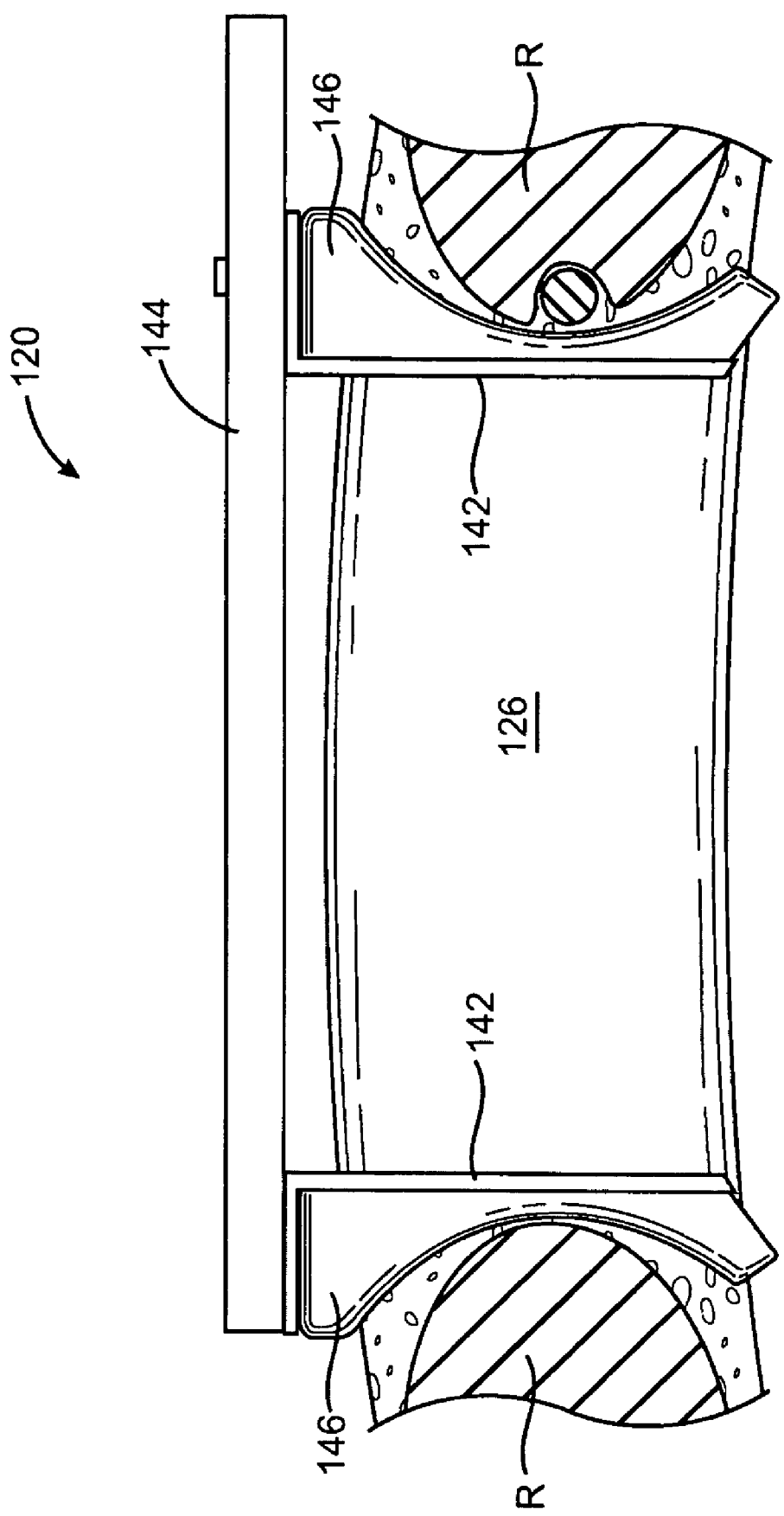
FIG. 4 shows a third embodiment of the retractor.

FIG. 4 shows a third embodiment of the retractor 140. In this embodiment, two discrete rigid blades 142 are mounted on a spreading track 144. Once the initial incision is made with the scalpel, the blades 142, located closely together on the spreading track 144, are inserted into the incision. The tissue contacting surface of the blades, in this case the outside surfaces, have a resilient surface 146 to non-traumatically engage the tissue. The resilient surface 146 may be a soft gel coating or a filled or an inflatable bladder containing or designed to contain air, gas, gel, silicone, saline or other material. Preferably, the retractor 140 includes a mechanism, for example a rack and pinion with a crank, can be used to forcibly separate the retractor blades 142 to create a space 148 for surgical access through the intercostal incision.

Alternatively, two or more blades 142 may be used to provide structural support for an inflatable ring 102, similar to the embodiment described in FIG. 1, in place of the resilient surface 146 in FIG. 4, such that the blades 142 would support the inflatable ring 102 to hold the ribs R and the inflatable ring 102 would protect the tissue from instruments being passed through the opening 148. For example, between 4 and 12 or more blades could be collapsably and releasably mounted on a ring or rod, similar in function to the spreading track 144 of FIG. 4. Once the ring or rod is in the incision, the blades 142 are deployed and the ring or rod could be removed. Then, the inflatable ring 102 located on the outer perimeter of the blades could be inflated to press against the tissue. Alternately, the inflatable ring 102 could be fully or partially inflated to provide protection for the tissue prior to deploying the blades. For especially delicate tissue or precise placement of the retractor, deployment could be accomplished in a series of stages where the inflatable ring 102 and blades 142 are alternately advanced outward.

Alternatively, a set of inflatable blades could be used alone or in combination with an inflatable bladder. The rigidity of the blades could be selected to be more or less than the bladder to provide more structural support. This could be accomplished by reinforcing the shape with stiffening elements or by using a greater inflation pressure in the blades.

The blade 142 may include a connector for holding one or more surgical or medical tools 128, as described above in connection with FIG. 3.

The retractor may be formed with a rigid metal frame that provides support for the inflatable retraction blades or surfaces. The metal frame may be an integrally formed wire mesh around which the inflatable portion(s) are formed. Alternatively, the frame may be used only during insertion of the inflatable member. Once in place, the retractor is inflated, thereby securing it within the percutaneous opening. At this point, the metal frame may be removed. The metal frame may be a mesh or a solid surface. The frame may be embedded into one of the walls of the inflatable member, or the inflatable member may be overmolded onto the frame.

Inflation of the bladder, blades or retractor may be accomplished by a manual or automatic pump.

To avoid overinflation, the bladder could be designed with a selected rupture pressure and/or pattern. In these cases, a medically safe material, such as saline, could be used.

While the present invention has been described herein with respect to the exemplary embodiments and the best mode for practicing the invention, it will be apparent to one of ordinary skill in the art that many modifications, improvements and subcombinations of the various embodiments, adaptations and variations can be made to the invention without departing from the spirit and scope thereof.

What is claimed is:

1. A method of surgical access comprising:
making an intercostal incision in a patient's thorax;
positioning a surgical retractor comprising an inflatable ring-shaped member in the intercostal incision;
engaging a first rib adjacent to the intercostal incision with a first concave surface on an outer surface of the inflatable ring-shaped member;
engaging a second adjoining rib adjacent to the intercostal incision with a second concave surface on the outer surface of the inflatable ring-shaped member;
inflating the inflatable ring-shaped member to open up an inner opening for surgical access through the surgical retractor and to separate the first rib and the second rib sufficiently to allow surgical access through the intercostal incision via the inner opening of the surgical retractor;
and supporting the inflatable ring-shaped member with a plurality of substantially rigid retractor blades positioned within the inner opening of the inflatable ring-shaped member.

2. The method of claim 1, wherein the inflatable ring-shaped member comprises a groove within at least one of the first concave surface and the second concave surface, and wherein the method further comprises positioning the groove so as to avoid applying pressure to an intercostal nerve adjacent to the intercostal incision when the inflatable ring-shaped member is inflated.

3. The method of claim 1, further comprising mounting the plurality of substantially rigid retractor on a substantially rigid ring or rod.

4. The method of claim 3, further comprising removing the substantially rigid ring or rod after positioning the plurality of substantially rigid retractor blades.

* * * * *